United States Patent
Mehta

(10) Patent No.: US 6,688,497 B2
(45) Date of Patent: Feb. 10, 2004

(54) APPARATUS AND METHOD FOR TISSUE RINSE

(76) Inventor: Ketan C. Mehta, 4077 Polled Hereford Dr., Santa Rosa, CA (US) 95404

( * ) Notice: Subject to any disclaimer, the term of this patent is extended or adjusted under 35 U.S.C. 154(b) by 0 days.

(21) Appl. No.: 10/367,586

(22) Filed: Feb. 14, 2003

(65) Prior Publication Data

US 2003/0160068 A1 Aug. 28, 2003

Related U.S. Application Data

(63) Continuation-in-part of application No. 09/845,759, filed on Apr. 30, 2001, now Pat. No. 6,520,384.

(51) Int. Cl.$^7$ .............................................. B65D 37/00
(52) U.S. Cl. ...................................... 222/211; 222/215
(58) Field of Search ..................... 222/207, 211–213, 222/215, 420–422; 141/22–24, 379–381

(56) References Cited

U.S. PATENT DOCUMENTS

| | | | |
|---|---|---|---|
| 2,571,921 A | 10/1951 | Morris | |
| 2,578,864 A | 12/1951 | Tupper | |
| 2,811,283 A | 10/1957 | Bowen | |
| 3,847,145 A | 11/1974 | Grossan | |
| 4,356,941 A | 11/1982 | McRoskey | |
| 4,489,535 A | 12/1984 | Veltman | |
| 4,513,891 A | 4/1985 | Hain et al. | |
| 4,925,128 A | 5/1990 | Brody | |
| 5,316,054 A | 5/1994 | Hall et al. | |
| 5,330,634 A | * 7/1994 | Wong et al. | 205/777.5 |
| 5,806,723 A | 9/1998 | DuBose | |
| 5,897,872 A | 4/1999 | Picciano | |
| 5,899,878 A | 5/1999 | Glassman | |

FOREIGN PATENT DOCUMENTS

| | | |
|---|---|---|
| DE | 296 02 605 U1 | 4/1996 |
| GB | 881807 | 11/1961 |
| WO | WO 96/29044 | 9/1996 |

OTHER PUBLICATIONS

NeilMed, "Sinus Rinse", 2000, London, XP–002207679, p. 7, 14.
Dr. Grossan Sinus Irrigator® Tip. Datasheet [online] Hydro Med Products, Jul. 19, 2000 [retrieved on Apr. 26, 2001]. Retrieved from the Internet: <URL:www.sinus–relief.com/whatsirr.html>.

(List continued on next page.)

Primary Examiner—J. Casimer Jacyna
(74) Attorney, Agent, or Firm—Fish & Richardson P.C.

(57) ABSTRACT

An apparatus and method for preparing a pH balanced saline solution and using the saline solution for rinsing tissue. The apparatus includes a container having flexible sidewalls and an opening for a removable cap. The cap has a rounded convex upper portion curving away from an opening at the cap's uppermost surface and has a conduit in the cap's interior, which conduit extends into the container when the apparatus is fully assembled or is connected to a tube that extends in the container. A saline solution is prepared by adding sodium chloride and sodium bicarbonate to distilled or boiled water. The sidewalls of the container are compressed to urge the saline solution through the conduit, or tube and conduit, and through the opening in the cap. The solution can be used to rinse tissue, such as a mucus membrane, eye tissue, skin or tissue inside an oral cavity.

8 Claims, 4 Drawing Sheets

OTHER PUBLICATIONS

SinuCleanse® ©2000. Datasheet [online] Med–Systems, Inc. Jan. 27, 2001 [retrieved on Jul. 10, 2001]. Retrieved from the Internet: <URL:www.sinucleanse.com/sinu2.html>.

Sinus–Rinse™ ©2001. Datasheet [online] SINUS–RINSE™ [retrieved on Jul. 10, 2001]. Retrieved from the Internet: <URL.www.sinusrinse.com>.

Using the Pulsatile Nasal Irrigator. Datasheet [online] Hydro Med Inc. Aug. 7, 2000 [retrieved on Apr. 27, 2001]. Retrieved from the Internet: <URL:www.ent–consult.com/nasal_irr_use.html>.

Breathe Ease ©2000. Datasheet [online] Hydro Med Inc. Apr. 16, 2000. 6 pages.

Entsol®, Datasheet [online], Retrieved from the Internet: <URL: www.entsolwash.com>. [undated; pre–Apr. 30, 2001].

"RhinoCare® Nasal Douche" brochure, Siemens & Co. (5 pages. English translation 12 pages.) (pre–Apr. 30, 2001).

Tomooka, Lance T., et al. "Clinical Study and Literature Review of Nasal Irrigation" *The Laryngoscope*, ©2000 The American Laryngological, Rhinological and Otological Society, Inc. pgs. 1189–1193, Jul. 2000.

Got a medical concern?—Ethicare—Nasal Irrigators™ 2001, Datasheet [online] Ethicare, Jan. 11, 2001, retrieved from the Internet: <URL www.ethicare.com>.

Rhinotip Irrigation Regimen ©2000, 1999. Datasheet [online] Comtech Solutions. Retrieved from the Internet: www.sinushealth.com.

Kehtan C. Mehta M.D., Sinus Rinse (A Complete Saline Nose Wash Kit), © NeilMed Products, 2000, Santa Rosa, CA.

\* cited by examiner

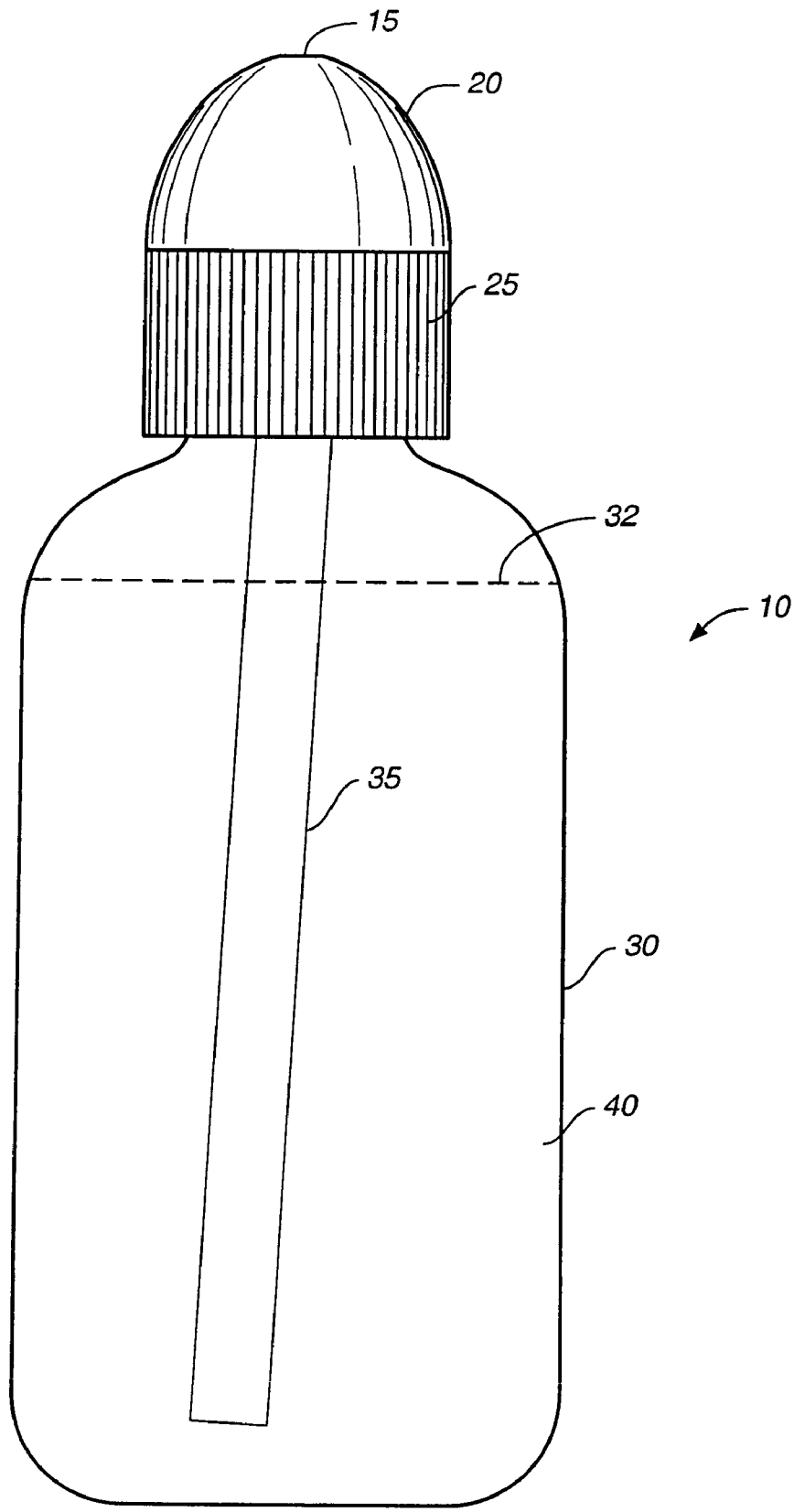
FIG._1

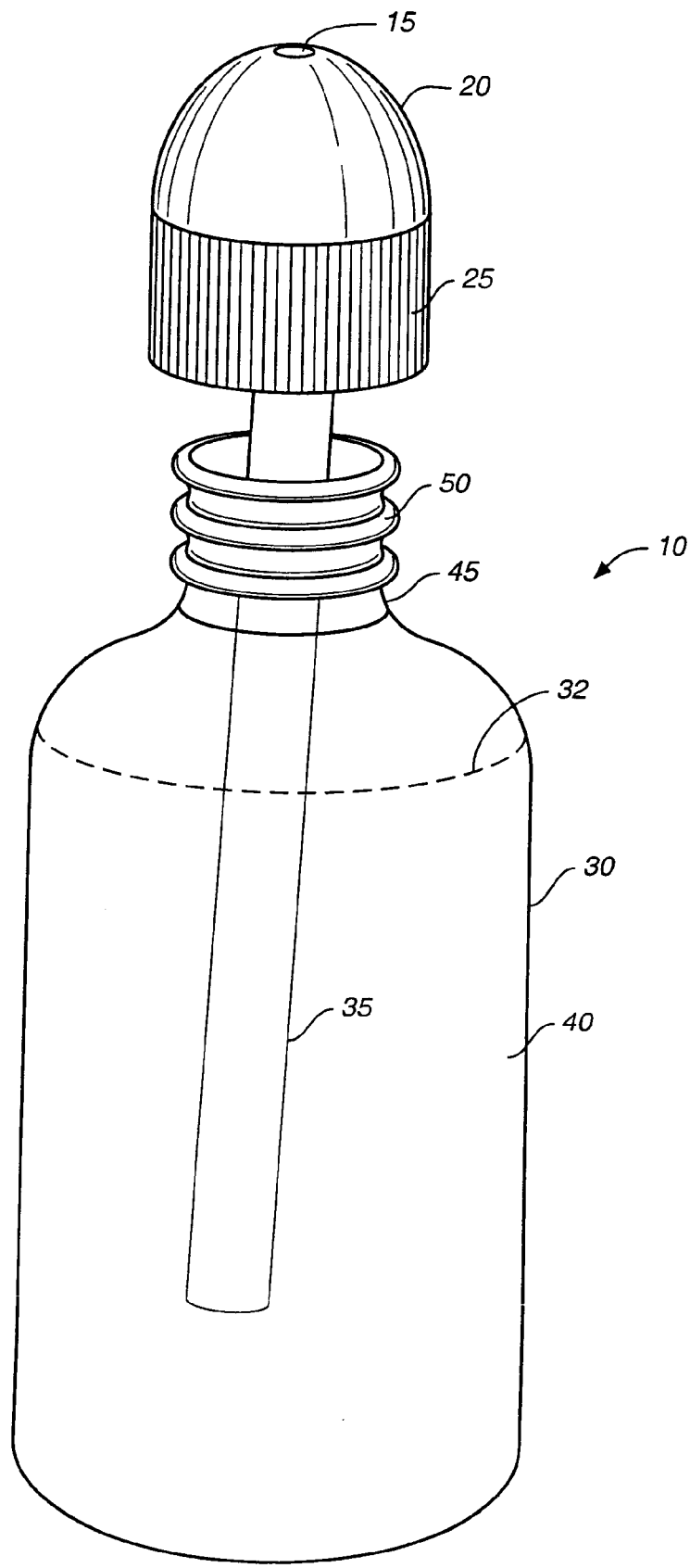
FIG._2

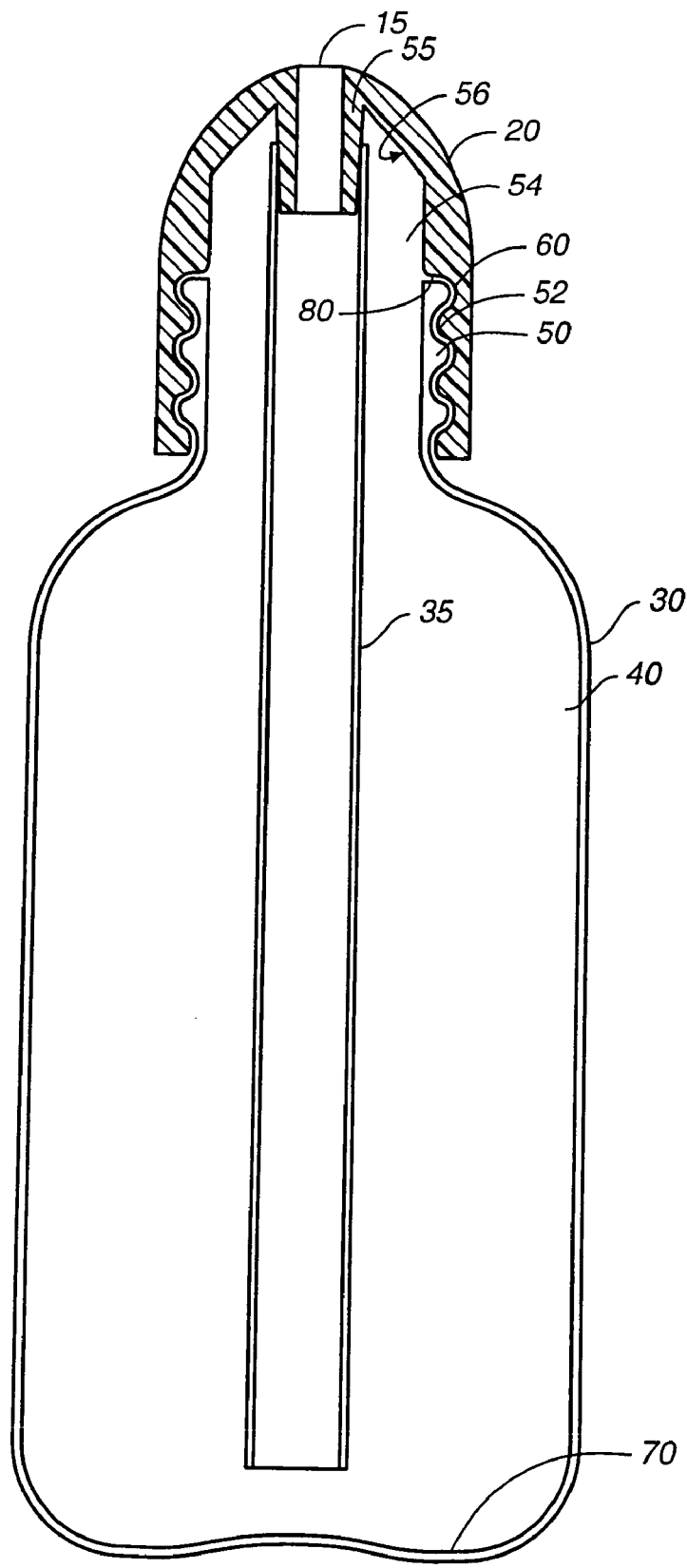
FIG._3

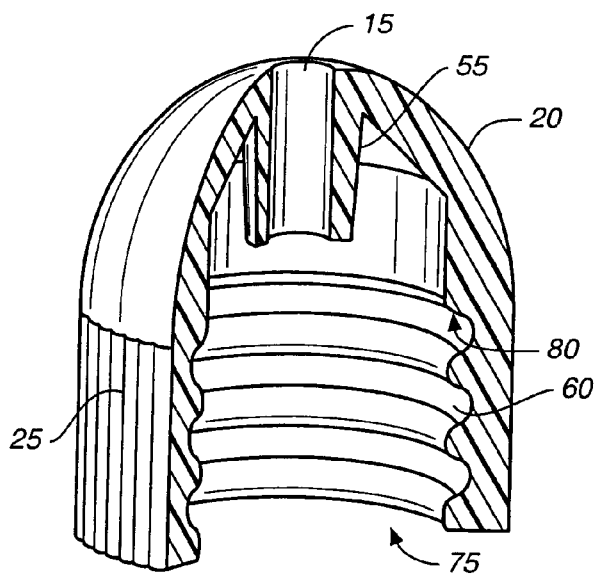
FIG._4
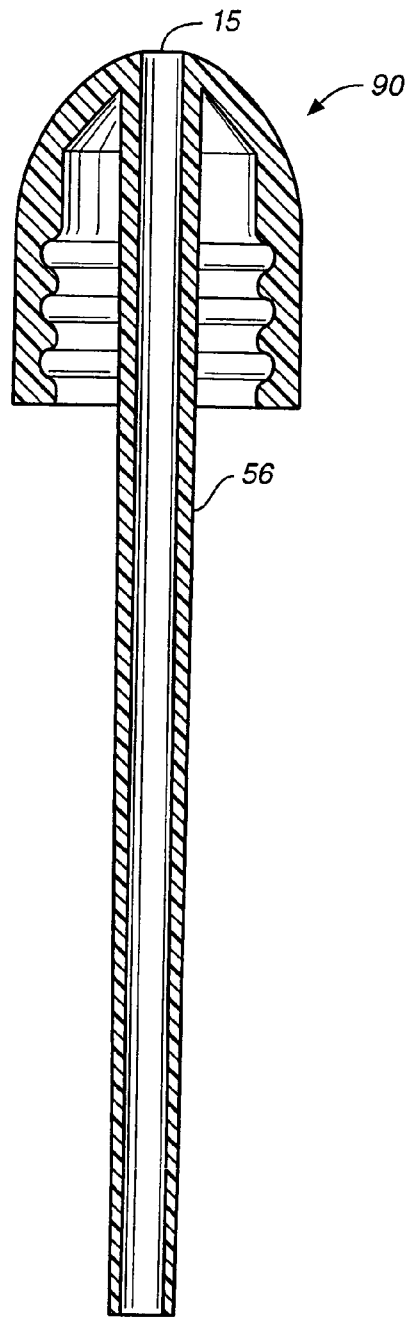
FIG._5

APPARATUS AND METHOD FOR TISSUE RINSE

CROSS REFERENCE TO RELATED APPLICATIONS

This is a continuation-in-part of U.S. Ser. No. 09/845,759, filed Apr. 30, 2001, now U.S. Pat. No. 6,520,384 which is incorporated by reference in its entirety and which is the basis of a claim of priority under 35 U.S.C. § 120.

TECHNICAL FIELD

This invention relates to methods and apparatus for rinsing tissues.

BACKGROUND

A body includes a number of sensitive tissues, for example, eye tissue, mucous membranes of the nasal passages and sinuses, and the interior of the mouth. These tissues are subject to bacterial growth, ulcers, irritation and disease.

Sinusitis is an inflammation of the mucosa of various sinuses, which are located around the nasal passages. Rhinitis is an inflammation of the mucosa of a nasal passage. Sinusitis and rhinitis can be caused by cold viruses, allergies to various allergens, smoking, bacterial or fungal infections, nasal polyps, deviated nasal septums and non-allergic hypersensitivities. Symptoms of rhinitis include: stuffy nose, runny or drippy nose, scratchy throat and dry cough. Symptoms of sinusitis are more severe than the symptoms of rhinitis. Acute and chronic sinusitis occurs when the sinuses are inflamed and the ostia, or passages, are blocked. Symptoms include: nasal congestion; runny or stuffy nose; white, yellow or green discharge; headache; night time cough; pain in the upper jaw or teeth; persistent fatigue; fever; loss of sense of smell or taste; and sometimes serious infections like meningitis, brain abscess or ear infections.

As indicated above, allergies can cause rhinitis and sinusitis. Allergens are organic particles that attach to the nasal mucosa or respiratory mucosa and lead to the development of an antibody, which subsequently creates a series of chemical reactions leading to symptoms. Every individual's reaction to allergen exposure is different. Indoor allergens include dust mites, mold, pet dander and cockroaches. Outdoor allergens include pollens, grass and mold. Other substances such as cigarette smoke, perfumes and aerosol sprays are irritants that can worsen allergy and sinus symptoms. Allergens can also irritate the eyes and cause itching, tearing, redness, and swelling of the eyelids.

There are various methods to treat the symptoms of, or to cure, sinus and ocular disease, including surgery. An effective nasal rinse can significantly reduce or permanently cure the symptoms of nasal allergies and sinus disease. Saline nasal irrigations have been used and mentioned in medical textbooks going back many years. A wide variety of techniques have been described, including swimming in salt water, which often results in some degree of inadvertent nasal salt water irrigation. For persons suffering from allergies irritating the eye, a saline solution can flush the allergens out of the eye.

Nasal rinsing or lavage is a treatment for rhinitis and sinusitis that uses a saline solution dispensed into the nasal passage to cleanse and wash away mucus and allergy creating particles and irritants. Lavaging allows the sinuses to drain normally and reduces the inflammation of the mucus membrane.

Oral rinsing with a saline solution can be used for therapeutic purposes. Similarly, a saline solution can also be used to relieve dry eyes, conjunctivitis, or flush foreign materials out of the eye, and can be used on a daily basis.

Prepared saline solution is available for uses including nasal lavage, oral rinse, and ocular drops, however a bottle filled with saline solution can be quite expensive. Alternatively, saline solution can be prepared at home using household ingredients. However, there is a concern for cleanliness and contamination, and for ensuring that the proper concentration level and acidity is achieved. Thus, there is a need for a method for preparing a saline solution having a consistent and appropriate concentration that is simple, inexpensive and not easily contaminated.

Nasal rinsing equipment currently available includes various types of dispensers that can be filled with a saline solution and which are then injected into the user's nasal passage. Conventional nasal rinsing equipment can be crude and may only be suitable for users having a certain size nostril. For proper use, the dispensing tip should comfortably seal against a user's nostril. Equipment having a dispenser tip designed for a certain size nostril can be useless for someone with a smaller nostril, in particular children, such as the nasal rinse equipment described in U.S. Pat. No. 5,806,723 for a DEVICE FOR LAVAGING. Thus, there is a need for equipment having a dispenser tip that effectively and comfortably seals against human nostrils of varying sizes, including nostrils of children.

Another problem with current nasal lavaging equipment is that the configuration of the dispensing tip can cause the saline solution to be dispensed into the nasal passage without sufficiently dispersing before reaching the back of the nasal passage, resulting in an uncomfortable or painful sensation for the user. There is a need for a dispenser tip configured to allow the saline solution to disperse sufficiently before reaching the back of the nasal passage.

Conventional lavaging equipment includes dispenser tips that are compatible with power operated oral irrigators. The dispenser tip and oral irrigator can be used to direct the irrigation solution to the mucus membrane of the mouth or throat. However, the dispenser tips are typically only compatible with a certain model of oral irrigator, such as the dispenser tip described in U.S. Pat. No. 3,847,145 for a NASAL IRRIGATION SYSTEM.

For the foregoing reasons, there is a need for an apparatus and system for preparing and dispensing a saline solution that is simple to use, capable of being prepared and administered in most any location, relatively inexpensive and suitable for use by persons having nostrils of varying sizes, and that is compatible with most commercially available oral irrigators.

SUMMARY

The present invention provides methods and apparatus for rinsing tissue with a saline solution. In general, in one aspect, the invention features a system for rinsing tissue that includes an iodine-free saline solution for rinsing tissue and an apparatus for dispensing the saline solution. The saline solution includes approximately 39 parts sodium chloride and approximately 1 to 2 parts sodium bicarbonate dissolved in water. The apparatus includes a cap and a container for holding the saline solution. The cap has a cylindrical lower portion; a rounded convex upper portion curving away from an axially aligned opening, from which a liquid is dispensed, located in the uppermost surface of the upper portion and curving downwardly to join the cylindrical lower portion; an open lower end; and a tubular conduit connected to the uppermost interior surface of the upper portion, the conduit having a hollow center axially aligned with the opening located in the upper portion. The container has flexible sidewalls and an axially aligned neck having an open end. The lower portion of the cap and the neck of the container are configured to join together with a liquid tight connection.

In general, in another aspect, the invention features a system for rinsing tissue, including a mixture for preparing a saline solution and an apparatus for dispensing the saline solution onto the tissue. The mixture includes approximately 39 parts sodium chloride and approximately 1 to 2 parts sodium bicarbonate, and is dissolved in water to form a pH balanced, iodine-free saline solution. The saline solution has a pH in the range of approximately 7.3 to 7.7.

In general, in another aspect, the invention features a method for rinsing tissue. The method includes preparing an iodine-free saline solution having a concentration in the range of approximately 0.9% to 1% by dissolving a measured amount of sodium chloride and sodium bicarbonate, the amount being approximately 39 parts sodium chloride and approximately 1 to 2 parts sodium bicarbonate, into a measured amount of water in a container with flexible sidewalls. The method further includes connecting a cap to the container. The cap has a cylindrical lower portion, a rounded convex upper portion curving away from an axially aligned opening from which a liquid is dispensed located in the uppermost surface of the upper portion and curving downwardly to join the cylindrical lower portion, an open lower end, and a tubular conduit connected to the uppermost interior surface of the upper portion and having a hollow center axially aligned with the opening located in the upper portion and wherein the conduit extends into the container. The sidewalls of the container are compressed to urge the saline solution out of the container and cause the saline solution to come in contact with the tissue.

In general, in another aspect, the invention features a method for rinsing tissue. The method includes preparing an iodine-free saline solution and dispensing the solution to rinse the tissue. The iodine-free saline solution has a concentration in the range of approximately 0.9% to 1%, and is prepared by mixing a measured amount of sodium chloride and sodium bicarbonate, the amount being approximately 39 parts sodium chloride and approximately 1 to 2 parts sodium bicarbonate, with a measured amount of water and dissolving the sodium chloride and sodium bicarbonate in the distilled water.

Implementations of the invention may include one or more of the following. The tissue can be a mucus membrane, eye tissue, skin, or tissue inside an oral cavity. The saline solution can be isotonic, and can have a saline concentration in the range of approximately 0.9% to 1%. The saline solution has a pH in the range of approximately 7.3 to 7.7. The exterior surface of the lower portion of cap can include rounded, vertical ridges. The opening in the cap can be between 2.5 mm and 4.25 mm in diameter. The conduit can have a slightly decreasing exterior diameter from the top to the bottom. The liquid tight connection between the cap and the neck can be a threaded connection. The container can have a marking to indicate the liquid level and be made of transparent material.

Advantages of the invention include one or more of the following. An apparatus is provided that can be used as a nasal rinse by children as well as adults. The apparatus includes a cap design that will provide an effective seal against the nostril of a child or adult. The cap can be used in conjunction with a power driven oral irrigator for performing a nasal, oral, or throat rinse. A flexible tube is provided that can be connected to most commercially available oral irrigators. The irrigation apparatus is simple to use, simple to clean, and inexpensive to replace. The user can inspect all parts of the apparatus to ensure cleanliness. Further, the user can sterilize the apparatus in the home using a microwave or boiling water to kill any bacteria on the surfaces of the apparatus.

A nasal or ocular rinse can be performed without having to bend the neck back and look upwards, as is the case with irrigation systems that rely on gravity to dispense the solution. This feature is particularly advantageous to persons who experience dizziness in this position, in particular elderly persons.

Another advantage of the rinse is that the mixture allows an iodine-free isotonic saline solution to be conveniently prepared that is pH balanced to the mucous membranes and tissue the solution would generally come into contact with. As such, the solution does not create a burning sensation when it comes in contact with said tissues. Generally, isotonic solutions are more comfortable and produce fewer negative sensations than hypotonic and hypertonic solutions when brought in contact with tissues. Greater comfort increases both patient tolerance of the rinsing solution and compliance with a course of treatment.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a side view of a dispenser assembly.

FIG. 2 is a side view of the dispenser assembly of FIG. 1 with the cap partially removed.

FIG. 3 is a cross-sectional view of the dispenser assembly of FIG. 1.

FIG. 4 is a cross-sectional view of the cap of FIG. 1.

FIG. 5 is a cross-sectional view of a cap with an extended conduit.

Like reference symbols in the various drawings indicate like elements.

DETAILED DESCRIPTION

Referring now to FIG. 1, an apparatus for performing a tissue rinse using a saline solution is shown. A dispenser assembly 10 includes a container 30, a cap 20 and a tube 35 connected to the interior portion of the cap 20 and extended into the container 30. The cap 20 can be removed from the container 30 by rotating the cap 20 (e.g., counter-clockwise), to allow the container 30 to be filled with a saline solution 40.

Referring now to FIGS. 2 through 4, the apparatus will be described in greater detail. The container 30 has flexible sidewalls that can be easily compressed by a hand to force the saline solution 40 through the tube 35 and through an opening 15 at the top of the cap 20, when the cap 20 is secured to the container 30. The uppermost portion of the container 30 includes a neck 45 that can include threads 50 to provide a tight connection to the cap 20 to prevent the escape of saline solution 40. However, attachment of cap 20 to container 30 can be accomplished in any convenient fashion that allows for removability and which maintains a liquid tight seal. Other methods for attachment can include a ring and groove assembly, a compression-fitting cap, exterior clamps or the like. The container 30 can include a marking 32 to indicate a liquid level. The marking 32 can be in any convenient form such as a printed line, a groove, a ring or the like. The container 30 can be made of a transparent material, such as a low-density polypropylene, so the amount of saline solution 40 is visible and the container 30 can be inspected for cleanliness. The container 30 should be able to withstand the heat of lukewarm to hot water and should be microwave safe to allow convenient heating of the contents of the container 30.

The cap 20 is hollow. The exterior of cap 20 has a cylindrically shaped lower portion and a conically shaped upper portion. The cap 20 has a lower opening 75 to secure cap 20 onto container 30 and an upper opening 15 at the apex of the conically shaped upper portion for expulsion of the saline solution 40 from the cap 20. The cylindrical lower portion of the exterior surface of cap 20 can include rounded, vertical ridges 25 to allow a user to grip the cap 20 when either securing the cap 20 onto, or removing the cap 20 from, the neck 45 of the container 30. If the user employs the apparatus for a nasal rinse, the conical upper portion of the exterior surface of cap 20 includes a smooth finish to allow a comfortable and effective seal against a user's nostril.

The exterior of the conical upper portion of cap 20 immediately slopes downward from opening 15 to the ridges 25. The exterior shape of a longitudinal cross-section of the upper portion of cap 20 can be a curve formed by the combination of at least three arcs. The uppermost portion of the curve can be an arc that is a portion of a circle having a first radius and the side portions of the curve can be arcs that are portions of a circle having a second radius. In the example of a cap 20 having a total height of substantially 40 mm and an exterior diameter at its widest point of substantially 29 mm, the first radius is substantially 10 mm and the second radius is substantially 30 mm. In another implementation, the exterior shape of a longitudinal cross-section of the upper portion of cap 20 can be elliptical.

The conical shape of the upper portion of cap 20 allows the cap 20 to be inserted into and sealed against the nostril of either a child or an adult, even though an adult typically has a relatively larger nostril. In the case of an adult, the cap 20 is inserted slightly further into the nasal passage before an effective seal is achieved.

The interior of cap 20 can form a first cylinder 52 extending from the lower surface of cap 20 to a height substantially one half of the total height of cap 20. The surface of substantially the lower quarter of the first cylinder 52 is smooth and the surface of the remainder of the first cylinder 52 can have threads 60 to permit a tight, threaded connection to the neck 45 of the container 30. The interior of cap 20 can form a second cylinder 54 extending from the top of the first cylinder 52 to a height substantially one quarter of the total height of cap 20. The second cylinder 54 has a smaller diameter than the first cylinder 54, thereby forming a lower surface 80 of the second cylinder 54, which lower surface 80 abuts the upper surface of the neck 45 of the container 30 when the cap 20 is secured onto container 30. The interior of cap 20 further forms a cavity having interior walls 56 slanting or curving from the top of the second cylinder 54 to the top of the exterior of a conduit 55 extending vertically downwards from opening 15.

The opening 15 leads into a conduit 55 that extends vertically from opening 15 downwards into the interior of cap 20. The exterior diameter of the conduit 55 gradually tapers from the diameter at the top of conduit 55 (closest to opening 15) to a lesser diameter at the bottom of conduit 55. The interior diameter remains substantially constant the entire length of the conduit 55. The tapered exterior of conduit 55 allows tube 35 to be forced over the top of the exterior of conduit 55 to form a snug fit. However, attachment of tube 35 to conduit 55 can be accomplished in any convenient fashion, including the addition of a ring (not shown) around the exterior of conduit 55 to effectively lock tube 35 onto conduit 55 once tube 35 is forced over the ring.

The diameter of opening 15 affects the flow rate of the saline solution 40 out of the cap 20. If the opening 15 is too small when the dispenser assembly 10 is used for nasal rinsing, the saline solution 40 will enter a user's nasal passage at such a velocity that the stream of saline solution 40 will not sufficiently disperse before reaching the rear wall of the user's nasal cavity and the force at which the saline solution 40 impacts the rear wall of the user's nasal cavity will cause a jabbing sensation. If the opening 15 is too large, the saline solution 40 will not exit the cap 20 with enough force to reach the rear wall of a user's nasal cavity. In one implementation, the diameter of opening 15 is made to be no larger than substantially 4.25 mm and no smaller than substantially 2.5 mm to allow the saline solution 40 to exit the cap 20 with enough force both to fully irrigate the nasal passage and to sufficiently disperse before reaching the rear wall of the user's nasal cavity to minimize any user discomfort. The conical shape of the upper portion of cap 20 allows an effective seal to be formed against a nostril being at least as large as the opening 15. The diameter of opening 15 is sized such that an effective seal can be formed against the nostril of a child as well as an adult.

The cap 20 can be constructed from a rigid plastic such as low-density polypropylene. Alternatively, cap 20 can be constructed from any other non-toxic rigid substance, including stainless steel. The cap 20 can be substantially 40 mm in height and have an exterior diameter at its widest point of substantially 29 mm.

When dispenser assembly 10 is fully assembled, tube 35 can be connected to conduit 55 and cap 20 is secured to container 30. Tube 35 extends into the interior of container 30, the lower surface of tube 35 being substantially half an inch above the base 70 of container 30. The tube can be made of a latex free, non-toxic, strong and flexible material such as polyurethane. For some purposes, such as eye irrigation where gravity can be relied upon, the dispenser assembly 10 can be used without the tube 35.

Referring now to FIG. 5, in another implementation, the cap and tube assembly can be a single unit. Cap 90 is similar in shape to cap 20, but modified such that conduit 56 extends a length comparable to the length of tube 35. The cap 90 can be made of a rigid plastic such as a low density polyethylene. Cap 90 can be connected to container 30 in the same manner as described above with reference to cap 20.

The dispenser assembly 10 can also include a plug or stopper (not shown) that fits into conduit 55 or conduit 56 through opening 15, to retain the saline solution 40 in the container 30 to permit transporting of the dispenser assembly 10 without leakage of the saline solution 40. The connection of the plug to cap 20 or cap 90 could be by any convenient means including a compression-fit or threaded connection.

The saline solution 40 can be prepared by dissolving sodium chloride (NaCl) and sodium bicarbonate (NaHCO$_3$) in water. Preferably distilled water is used, but purified or clean tap water can also be used. If purified or clean tap water is used, it can be boiled. Boiled tap water typically has a pH of anywhere between 6 and 8. Distilled water typically has a pH of below 6.5 Preparing a saline solution as described below yields a solution having a pH in the range of approximately 7 to 8, with variations due to the pH of the water used to prepare the solution, which as stated above can vary between 6 and 8. Preferably distilled water is used and a saline solution having a pH in the range of approximately 7.3 to 7.7 is prepared. The saline solution is therefore pH balanced to human tissue, which typically has a pH of 7.4.

Packets containing a mixture of NaCl and $NaHCO_3$ for preparing an isotonic saline solution pH balanced to human tissue are available from NeilMed™ Products located in Santa Rosa, Calif. One packet size available contains approximately a 2.16 gram mixture of substantially 39 parts NaCl and 1 to 2 parts $NaHCO_3$, and can be used to prepare an isotonic saline solution having a concentration of approximately 0.9% to 1%, by dissolving the contents of the packet into approximately 8 ounces of distilled water. The same proportions of NaCl to $NaHCO_3$ can conversely be described as approximately 19.5 to 39 parts NaCl to 1 part $NaHCO_3$. A hypertonic saline solution can be prepared by dissolving more than one packet of the $NaCl/NaHCO_3$ mixture into approximately 8 ounces of distilled water, or by mixing one packet with less than 8 ounces of water. A hypotonic solution can be prepared either mixing less than one packet of the $NaCl/NaHCO_3$ mixture into approximately 8 ounces of water, or mixing one packet with more than 8 ounces of water.

Hypotonic, hypertonic, or isotonic saline solutions can be used for rinsing and lavaging, with varying levels of comfort for the user depending on the saline content of the solution. Negative sensations can be caused by a saline solution prepared using home ingredients, such as table salt, which results in a more acidic solution that can cause burning. The $NaCl/NaHCO_3$ packets described above contain all natural and iodine free ingredients and form an isotonic saline solution that is pH balanced to human tissue the saline solution could typically come into contact with. Such a "pH balanced" solution that is compatible with the human tissue prevents burning or stinging during lavage or rinsing, An aluminum lining can be used inside the packets to protect the contents from moisture, which can adversely affect the ease with which the $NaCl/NaHCO_3$ dissolves in the water. A dotted line can be marked on the exterior of the packet to provide a guide for cutting open the packet.

The dispenser assembly 10 and saline solution 40 can be used to perform a nasal, oral, throat or ocular rinse. Using the method described below, a user of the dispenser assembly 10 can irrigate human tissue, such as a nasal passage, oral cavity, throat or eye, to remove mucus, allergens, and irritants. Starting with the cap 20 removed from the container 30, the container 30 is filled with approximately eight ounces of water. A dashed line marked on the exterior of container 30 indicates to a user when eight ounces of fluid has been poured into the container 30. The water can then be warmed in a microwave oven. The water can be warmed using five-second increments to avoid excessive heating. If the water is heated to hotter than lukewarm, it is recommended to allow the water to cool before proceeding. Alternatively, the water can be warmed before pouring it into container 30 or does not have to be warmed at all.

A packet containing the $NaCl/NaHCO_3$ mixture is cut open along the dotted line and emptied into the container 30. The cap 20 having the tube 35 connected to the conduit 55 is secured onto the container 30 by aligning the threads 60 of cap 20 with the threads 50 of neck 45 and screwing the cap 20 onto the neck 45 by gripping the ridges 25 and rotating the cap 20 clockwise until fully tightened. The dispenser assembly 10 is shaken until the $NaCl/NaHCO_3$ mixture is fully dissolved in the distilled water.

To rinse a nasal passage, the user bends forward to a comfortable level, tilting the head slightly down and applies the cap 20 snugly against the left nostril with opening 15 directed into the left nasal passage. The container 30 is squeezed to force the saline solution 40 to enter the left nasal passage. The process is repeated applying the cap snugly against the right nostril. The saline solution 40 that was injected into the nasal passages will drain from the nasal passages or the mouth and should not be swallowed by the user. The user then gently blows the nose. Any unused portion of the saline solution 40 is discarded and the dispenser assembly 10 is cleaned. A nasal rinse can be performed once or twice a day or as recommended by a qualified physician.

For oral irrigation, the user directs the saline solution 40 toward the desired location in the mouth. The user then expels the excess solution after the rinse has been employed. The user can also squeeze the saline solution 40 into the mouth from the container 30 until the user has a mouthful of saline solution 40. The saline solution 40 can be swished within the mouth. To rinse the throat, the user directs the apparatus towards the back of the throat and squeezes the container 30 to force the saline solution 40 towards the throat. Alternatively, the user can take the solution from a cup or mug. A user who is unable to take the solution on their own can have the solution placed in his or her mouth with an apparatus, such as, for example, a straw or oral syringe. The user can then gargle or swish the solution in the mouth or throat. The user then expels the saline solution 40. Users unable to expel on their own can have the solution suctioned from their mouth and throat with an aspirator. Oral irrigation can be performed at regular intervals to relieve irritation, discomfort or foreign substances from the mouth and throat.

Oral irrigation can be performed after meals, after tooth brushing or as recommended by a qualified physician or dentist. Persons with immunosuppressed conditions, severe systemic disease, or cancer should maintain oral hygiene to prevent septimecia and control oral complications related to their condition. Oral rinsing can aid in maintaining good oral hygiene, and can also be prescribed for treatment of periodontal disease, such as, acute and chronic gingivitis or gum infections, treatment of tongue infections, application post-surgery, promotion of post-trauma tissue healing or treatment of oral lesions. Moreover, oral and nasal rinsing aids in clearing bacteria from the mouth, throat and nose from healthy individuals. Bacteria that generally reside in the mouth make-up the normal oral flora. An abundance of bacteria can cause aspiration of bacteria into the lungs, which can subsequently lead to pneumonia and pneumonia related complications.

Throat irritation caused by allergies or illness can be relieved by rinsing with the saline solution. Oral irrigation can be used to clear food debris, dried mucus, pus at the site of ulcers, dead tissue, bacterial and fungal colonies, blood clots and other organic or inorganic substances that impede the maintenance of a healthy system. Cleaning these substances out of the mouth can also improve the odor of the breath.

For rinsing an eye, the dispenser assembly 10 can be used without the tube 35. The user tilts his or her head back to facilitate the acceptance of saline solution 40 into the eye.

The user can gently pull downward on the lower lid of the eye with a finger. With the other hand, he or she then inverts the dispenser assembly 10 and squeezes out the saline solution to force drops from the opening 15 into the eye. The opening can be directed at any part of the eye, such as toward the conjuctiva, the sclera, or the opening formed by pulling down on the lower eyelid. Ocular irrigation can clear foreign substances from the eye and provide relief from eye irritation. Clearing foreign substances from the eye for example, such as, particles or chemicals, can prevent further damages resulting from lack of treatment. Other uses, such as for rinsing open wounds, can be achieved by directing the cap 20 of the dispenser assembly 10 at the tissue, and squeezing the container 30 to release the saline solution 40.

In addition to human health care, animals can benefit from the use of saline solutions. Dogs, cats and other animals suffer from ailments which can be treated in a similar fashion to human ailments. Therefore, a saline solution can be used to maintain or improve the health of non-human animals.

The cap 20, tube 35 and container 30 should be thoroughly cleaned after each use. The cap 20 can be sterilized by submersing it briefly in boiling water. The tube can be cleaned by rinsing the tube thoroughly with water and using a narrow brush to clean the interior, such as the type of brush commercially available for cleaning baby bottles. The container 30 can similarly be cleaned by rinsing the container 30 with water and using an appropriately-sized brush. A vinegar and water solution can also be used to clean the dispenser assembly 10. Alternatively, the user can rinse the apparatus with an anti-bacterial solution, appropriate solutions can include a high concentration of isopropyl alcohol or an equivalent anti-bacteria ingredient.

An alternative lavaging technique includes using a power operated water jet dispenser designed for oral irrigation attached to a dispenser tip suitable for nasal or oral irrigation. An oral irrigator such as the Waterpik® Oral Irrigator manufactured by The Waterpik Technologies Personal Healthcare Products Division of Water Pik Technologies, Inc., based in Fort Collins, Colo., can be used in conjunction with cap 20 and tube 35 to perform a nasal lavage. Tube 35 has an inner diameter such that it can form a snug fit connection to a water tube (not shown) forming part of the oral irrigator. The flexibility of tube 35 permits compatibility to most commercially available oral irrigators. The water reservoir element of the oral irrigator is filled with a saline solution that can be prepared using the method described above. The oral irrigator can then be operated to drive the saline solution through the water tube into tube 35 and out of opening 15 into a user's nasal passage, oral cavity or throat.

Cap 90 can also be used in conjunction with an oral irrigator as described above. A length of flexible tubing (not shown) can be used as a coupling between conduit 56 and a water tube forming part of the oral irrigator.

A number of embodiments of the invention have been described. Nevertheless, it will be understood that various modifications may be made without departing from the spirit and scope of the invention. Accordingly, other embodiments are within the scope of the following claims.

What is claimed is:

1. A method for rinsing eye tissue, the method comprising:
   preparing an iodine-free saline solution having a concentration in the range of approximately 0.9% to 1% by dissolving a measured amount of sodium chloride and sodium bicarbonate, the amount being approximately 39 parts sodium chloride and approximately 1 to 2 parts sodium bicarbonate, into a measured amount of water in a container, wherein the container has flexible sidewalls;
   connecting a cap having:
      a cylindrical lower portion,
      a rounded convex upper portion curving away fron an axially aligned opening from which a liquid is dispensed located in the uppermost surface of the upper portion and curving downwardly to join the cylindrical lower portion,
      an open lower end, and
      a tubular conduit connected to the uppermost interior surface of the upper portion and having a hollow center axially aligned with the opening located in the upper portion and wherein the conduit extends into the container; and
   compressing the sidewalls of the container to urge the saline solution out of the container and causing the saline solution to come in contact with the eye tissue.

2. The method of claim 1, wherein the saline solution has a pH in the range of approximately 7.3 to 7.7.

3. A method for rinsing tissue located inside an oral cavity, the method comprising:
   preparing an iodine-free saline solution having a concentration in the range of approxixnately 0.9% to 1% by dissolving a measured amount of sodium chloride and sodium bicarbonate, the amount being approximately 39 parts sodium chloride and approximately 1 to 2 parts sodium bicarbonate, into a measured amount of water in a container, wherein the container has flexible sidewalls;
   connecting a cap having:
      a cylindrical lower portion,
      a rounded convex upper portion curving any from an axially aligned opening from winch a liquid is dispensed located in the uppennost surface of the upper portion and curving downwardly to join the cylindrical lower portion,
      an open lower end, and
      a tubular conduit connected to the uppermost interior surface of the upper portion and having a hollow center axially aligned with the opening located in the upper portion and wherein the conduit extends into the container; and
   compressing the sidewalls of the container to urge the saline solution out of the container and causing the saline solution to come in contact wit the tissue located inside an oral cavity.

4. The method of claim 3, wherein the saline solution has a pH in the range of approximately 7.3 to 7.7.

5. A method for rinsing eye tissue, the method comprising:
   preparing an iodine-free saline solution having a concentration in the range of approximately 0.9% to 1% by mixing a measured amount of sodium chloride and sodium bicarbonate, the amount being approximately 39 parts sodium chloride and approximately 1 to 2 parts sodium bicarbonate, with a measured amount of distilled water and dissolving the sodium chloride and sodium bicarbonate in the water; and
   dispensing the saline solution to rinse the eye tissue.

6. The method of ciaim 5, wherein the saline solution has a pH in the range of approximately 7.3 to 7.7.

7. A method for rinsing tissue located inside an oral cavity, the method comprising:

preparing an iodine-free saline solution having a concentration in the range of approximately 0.9% to 1% by mixing a measured amount of sodium chloride and sodium bicarbonate, the amount being approximately 39 parts sodium chloride and approximately 1 to 2 parts sodium bicarbonate, with a measured amount of distilled water and dissolving the sodium chloride and sodium bicarbonate in the water; and dispensing the saline solution to rinse the tissue located inside an oral cavity.

8. The method of claim 7, wherein the saline solution has a pH in the range of approximately 7.3 to 7.7.

* * * * *

UNITED STATES PATENT AND TRADEMARK OFFICE
CERTIFICATE OF CORRECTION

PATENT NO.   : 6,688,497 B2
DATED        : February 10, 2004
INVENTOR(S)  : Ketan C. Mehta It is certified that error appears in the above-identified patent and that said Letters Patent is hereby corrected as shown below:

<u>Column 10,</u>
Line 28, replace "range of approxixnately 0.9% to 1%" with -- range of approximately 0.9% to 1% --
Line 37 replace "a rounded convex upper portion curving any from" with -- a rounded convex upper portion curving away from --
Line 39, replace "located in the uppennost surface" with -- located in the uppermost surface --

Signed and Sealed this

Ninth Day of November, 2004

JON W. DUDAS
*Director of the United States Patent and Trademark Office*